(12) United States Patent
Ono

(10) Patent No.: US 8,421,034 B2
(45) Date of Patent: Apr. 16, 2013

(54) FLUOROSCOPY APPARATUS AND FLUORESCENCE IMAGE PROCESSING METHOD

(71) Applicant: Olympus Corporation, Tokyo (JP)

(72) Inventor: Fumiko Ono, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/646,169

(22) Filed: Oct. 5, 2012

(65) Prior Publication Data

US 2013/0026390 A1    Jan. 31, 2013

Related U.S. Application Data

(63) Continuation of application No. PCT/JP2011/058780, filed on Apr. 7, 2011.

(30) Foreign Application Priority Data

Apr. 12, 2010   (JP) ................................ 2010-091431

(51) Int. Cl.
  *G01J 1/58*   (2006.01)
(52) U.S. Cl.
  USPC ................................. 250/458.1; 250/459.1
(58) Field of Classification Search ............... 250/252.1, 250/458.1, 459.1
  See application file for complete search history.

(56) References Cited

U.S. PATENT DOCUMENTS

| 2006/0025692 A1 | 2/2006 | Ishihara |
| 2010/0059690 A1 | 3/2010 | Ishihara |

FOREIGN PATENT DOCUMENTS

| JP | 62-247232 A | 10/1987 |
| JP | 07-246184 A | 9/1995 |
| JP | 08-224209 A | 9/1996 |
| JP | 2006-61683 A | 3/2006 |
| JP | 2008-173290 A | 7/2008 |

OTHER PUBLICATIONS

International Search Report dated Jul. 5, 2011 issued in PCT/JP2011/058780.

*Primary Examiner* — Mark R Gaworecki
(74) *Attorney, Agent, or Firm* — Scully Scott Murphy & Presser, PC

(57) ABSTRACT

Provided is a fluoroscopy apparatus comprising a white-light-image generating section that generates a white-light image of observation target, a fluorescence-image generating section that generates a fluorescence image of the observation target, a fluorescence-image correcting section that normalizes the fluorescence image with the white-light image, a displacement calculating section that calculates the displacement of the observation target from a plurality of white-light images generated at time intervals, a region-size calculating section that calculates the size of a region having a fluorescence intensity higher than or equal to a predetermined threshold value from the fluorescence image, and a control unit that controls the fluorescence-image correcting section so that, when the displacement of the observation target relative to the size of the region is larger than or equal to a predetermined proportion, normalization of the fluorescence image is stopped.

5 Claims, 7 Drawing Sheets

| LEVEL | 1 | 2 | 3 | 4 | 5 | 6 |
|---|---|---|---|---|---|---|
| THRESHOLD VALUE S | 0 | 1/10 | 1/5 | 3/10 | 2/5 | 1/2 | they# FLUOROSCOPY APPARATUS AND FLUORESCENCE IMAGE PROCESSING METHOD

CROSS REFERENCE TO RELATED APPLICATIONS

This is a continuation of International Application PCT/JP2011/058780, with an international filing date of Apr. 7, 2011, which is hereby incorporated by reference herein in its entirety. This application claims the benefit of Japanese Patent Application No. 2010-091431, the content of which is incorporated herein by reference.

TECHNICAL FIELD

The present invention relates to a fluoroscopy apparatus and a fluorescence image processing method.

BACKGROUND ART

A known fluoroscopy apparatus in the related art normalizes the intensity of fluorescence coming from a fluorescent material that preferentially accumulates in a lesion, such as a tumor, present in biological tissue by using the intensity of reflected light at the surface of the same biological tissue (for example, see PTL 1).

CITATION LIST

Patent Literature

{PTL 1} Japanese Unexamined Patent Application, Publication No. SHO 62-247232

SUMMARY OF INVENTION

Solution to Problem

A first aspect of the present invention is a fluoroscopy apparatus comprising a white-light-image generating section that generates a white-light image from a signal obtained by image-capturing reflected light of white light that irradiates an observation target; a fluorescence-image generating section that generates a fluorescence image from a signal obtained by image-capturing fluorescence generated by irradiation of the observation target with excitation light; a fluorescence-image correcting section that normalizes the fluorescence image generated by the fluorescence-image generating section by using the white-light image generated by the white-light-image generating section; a displacement calculating section that calculates the displacement of the observation target in the white-light image by processing a plurality of the white-light images generated by the white-light-image generating section from signals obtained by image-capturing at time intervals; a region-size calculating section that calculates the size of a region having a fluorescence intensity higher than or equal to a predetermined threshold value by processing the fluorescence image generated by the fluorescence-image generating section; and a control unit that controls the fluorescence-image correcting section so that normalization of the fluorescence image is stopped when the displacement of the observation target calculated by the displacement calculating section relative to the size of the region calculated by the region-size calculating section is higher than or equal to a predetermined proportion.

A second aspect of the present invention is a fluorescence image processing method, comprising a white-light-image generation step of generating a white-light image from a signal obtained by image-capturing reflected light of white light that irradiates an observation target; a fluorescence-image generation step of generating a fluorescence image from a signal obtained by image-capturing fluorescence generated by irradiation of the observation target with excitation light; a region-size calculation step of calculating the size of a region having a fluorescence intensity higher than or equal to a predetermined threshold value by processing the fluorescence image generated in the fluorescence-image generation step; a displacement calculation step of calculating the displacement of the observation target in the white-light image by processing a plurality of the white-light images generated from signals obtained by image-capturing at time intervals; and a fluorescence-image correction step of normalizing the fluorescence image by using the white-light image only when the displacement of the observation target calculated in the displacement calculation step relative to the size of the region calculated in the region-size calculation step is lower than a predetermined proportion.

DESCRIPTION OF EMBODIMENTS

Figure 1:
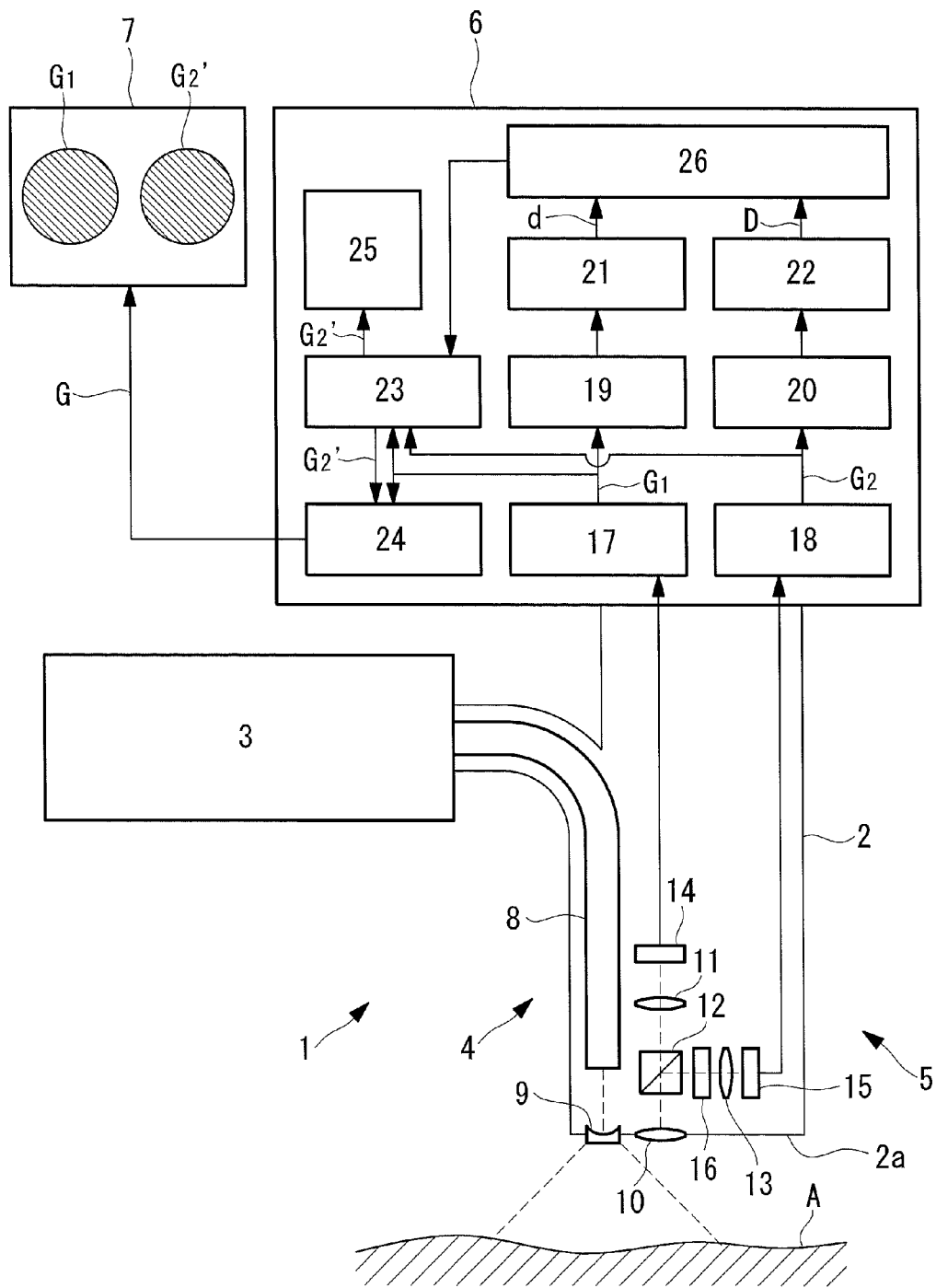
FIG. 1 is block diagram illustrating a fluoroscopy apparatus according to an embodiment of the present invention.

A fluoroscopy apparatus 1 according to an embodiment of the present invention and a fluorescence image processing method will be described hereinbelow with reference to the drawings.

The fluoroscopy apparatus 1 according to this embodiment is a fluorescence endoscope apparatus and is equipped with a long, thin inserted portion 2 to be inserted into a body, a light source unit 3 that emits white light and excitation light, an illumination unit 4 that radiates the white light and the excitation light emitted from the light source unit 3 toward an observation target A through the distal end of the inserted portion 2, an image acquisition unit 5 that is provided at the distal end of the inserted portion 2 and that acquires image information of biological tissue serving as the observation target A, an image processing unit 6 that is disposed at the base end of the inserted portion 2 and that processes the image information acquired by the image acquisition unit 5, and a monitor 7 that displays an image G processed by the image processing unit 6.

The illumination unit 4 is disposed along substantially the entire length of the inserted portion 2 in the longitudinal direction and includes a light guide fiber 8 that guides the white light and the excitation light emitted from the light source unit 3 and an illumination optical system 9 that is provided at the distal end of the inserted portion 2 and that spreads the white light and the excitation light guided by the light guide fiber 8 and shines them onto the observation target A facing a distal end face 2a of the inserted portion 2.

The image acquisition unit 5 includes an objective lens 10 that collects return light returning from a predetermined observation range of the observation target A, a dichroic mirror 12 that reflects light having a wavelength larger than or equal to an excitation wavelength (excitation light and fluorescence) of the return light collected by the objective lens 10 and that allows white light having a wavelength shorter than the excitation wavelength to pass therethrough, two focusing lenses 11 and 13 that focus the white light that has passed through the dichroic mirror 12 and the fluorescence reflected by the dichroic mirror 12, respectively, and two image-acquisition devices 14 and 15, such as CCDs, that image-capture the white light and the fluorescence focused by the focusing lenses 11 and 13, respectively. In the drawing, reference sign 16 denotes an excitation-light cut filter that blocks the excitation light of the light reflected by the dichroic mirror 12.

As shown in FIG. 1, the image processing unit 6 includes a white-light-image generating section 17 that sequentially generates white-light images $G_1$ from white-light image signals acquired at time intervals by the image-acquisition device 14, a fluorescence-image generating section 18 that sequentially generates fluorescence images $G_2$ from fluorescence image signals acquired at time intervals by the image-acquisition device 15, a white-light-image storage section 19 that sequentially stores the white-light images $G_1$ generated sequentially by the white-light-image generating section 17, and a fluorescence-image storage section 20 that sequentially stores the fluorescence images $G_2$ generated sequentially by the fluorescence-image generating section 18.

The image processing unit 6 further includes a displacement calculating section 21 that calculates the displacement d of the observation target A relative to the distal end face 2a of the inserted portion 2 from the white-light images $G_1$ stored in the white-light-image storage section 19 and a region-size calculating section 22 that extracts a region that is suspected of being a lesion site from the fluorescence images $G_2$ stored in the fluorescence-image storage section 20 and that calculates the size (region size) D thereof.

The image processing unit 6 further includes a normalization computing section 23 that normalizes the fluorescence images $G_2$ by using the white-light images $G_1$ generated by the white-light-image generating section 17 and the fluorescence images $G_2$ generated by the fluorescence-image generating section 18, an image combining section 24 that combines the normalized fluorescence images (hereinafter also referred to as normalized fluorescence images) $G_2'$ with the white-light images $G_1$, and a normalized-image storage section 25 that stores the normalized fluorescence images $G_2'$.

The image processing unit 6 further includes a control unit 26 that controls the normalization computing section 23 by determining whether to normalize the fluorescence images $G_2$ by the normalization computing section 23 on the basis of the displacement d calculated by the displacement calculating section 21 and the region size D calculated by the region-size calculating section 22.

The displacement calculating section 21 extracts common feature points (for example, high-brightness region) of two continuous white-light images $G_1$ acquired at time intervals corresponding to the observation period and obtains the distance between the extracted feature points to thereby calculate the relative displacement d between the distal end face 2a of the inserted portion 2 and the observation target A during the time the two white-light images $G_1$ are acquired.

Figure 2:
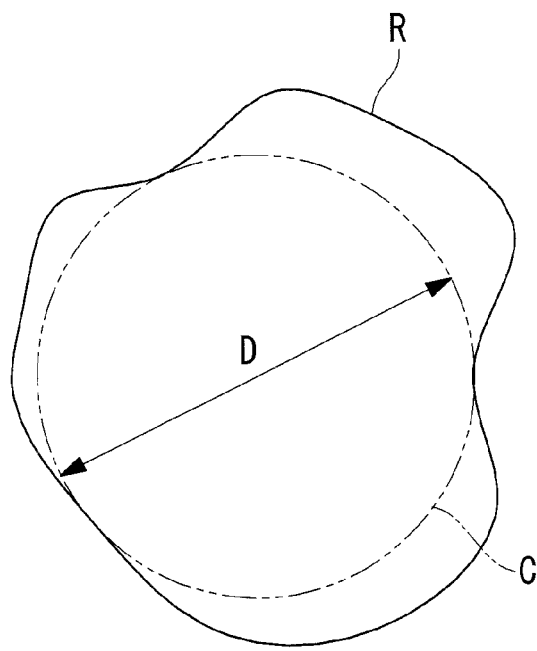
FIG. 2 is a diagram explaining a high-fluorescence-brightness region of a fluorescence image acquired by the fluoroscopy apparatus in FIG. 1 and the diameter of an inscribed circle, indicating the size thereof.

The region-size calculating section 22 extracts a region (high-fluorescence-brightness region) R having a fluorescence brightness higher than or equal to a predetermined threshold value by binarizing the fluorescence images $G_2$ with the predetermined threshold value and calculates the diameter of a circle C inscribed in the region R as the region size D of the high-fluorescence-brightness region R, as shown in FIG. 2.

The control unit 26 receives the displacement d calculated by the displacement calculating section 21 and the region size D of the high-fluorescence-brightness region R calculated by the region-size calculating section 22 and calculates the proportion of the displacement d to the region size D, d/D, and if the proportion d/D is higher than or equal to a predetermined proportion, stops the normalization computation of the fluorescence images $G_2$ by the normalization computing section 23, and only when the proportion d/D is lower than the predetermined proportion, allows the normalization computing section 23 to perform the normalization computation of the fluorescence images $G_2$.

Figure 4:
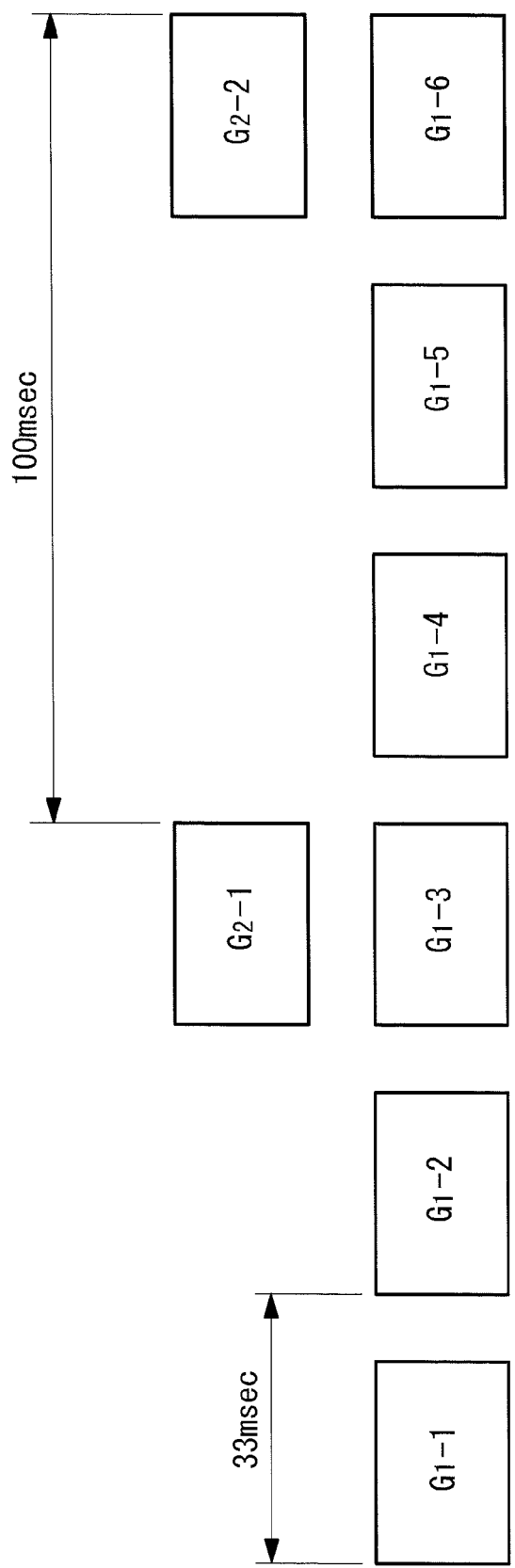
FIG. 4 is a diagram illustrating the timing at which fluorescence images and white-light images are acquired by the fluoroscopy apparatus in FIG. 1.

For example, as shown in FIG. 4, if the exposure time of each of the white-light images $G_1$ (−1 to −6) is 33 msec, and the exposure time of each of the fluorescence images $G_2$ is 100 msec, three white-light images $G_1$ and one fluorescence image $G_2$ are acquired during an observation period of 100 msec. In this embodiment, the normalization computation of the fluorescence images $G_2$ is performed using fluorescence images $G_2$–1 and $G_2$–2 and white-light images $G_1$–3 and $G_1$–6 acquired every observation period.

Figure 3:
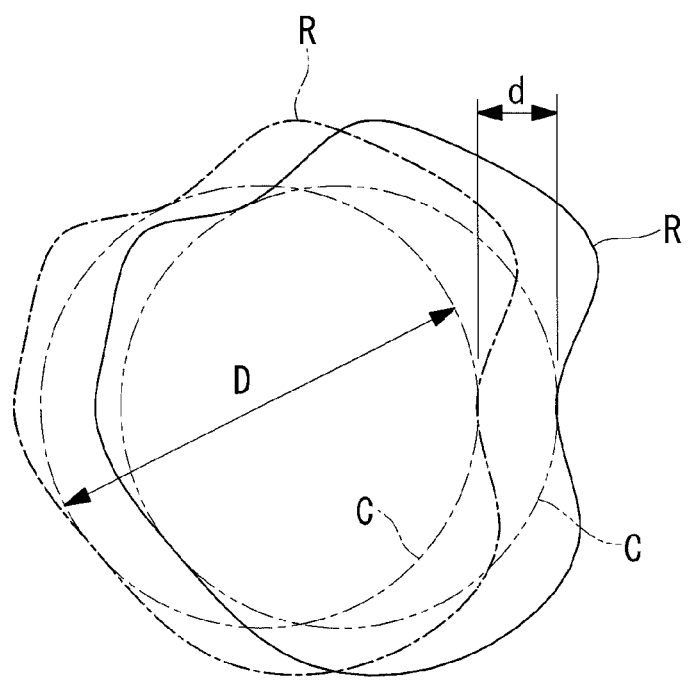
FIG. 3 is a diagram illustrating the displacement of the high-fluorescence-brightness region in FIG. 2.

Here, provided that the fluorescence images $G_2$ and the white-light images $G_1$ overlap by substantially half of the high-fluorescence-brightness region R that is suspected of being a lesion site, a shift of up to half of the region size D of the high-fluorescence-brightness region R between the white-light images $G_1$ acquired every third image is considered to be permitted to ensure sufficient precision of normalization. That is, the precision of normalization is considered to be maintained when the displacement d shown in FIG. 3 is ½D or less during about 100 msec, where D is the diameter of a circle that indicates the region size D.

Thus, the control unit 26 determines whether the proportion of the displacement d to the region size D of the fluorescence images $G_2$ is ½ or less, and if it is ½ or less, permits normalization by the normalization computing section 23, and if it is higher than ½, disables normalization by the normalization computing section 23.

If normalization is permitted by the control unit 26, the normalization computing section 23 calculates the normalized fluorescence image $G_2'$ by dividing the fluorescence image $G_2$ input from the fluorescence-image generating section 18 by the white-light image $G_1$ input from the white-light-image generating section 17. The image combining section 24 generates a combined image G in which the white-light image $G_1$ sent from the white-light-image generating section 17 and the normalized fluorescence image $G_2'$ output from the normalization computing section 23 are arranged side-by-side (or superimposed) and outputs the combined image G to the monitor 7. In the case where the normalized fluorescence image $G_2'$ is to be superimposed on the white-light image $G_1$, it is desirable to color a region, of the normalized fluorescence image $G_2'$, having brightness value higher than a predetermined threshold value in blue or the like, and to superimpose the normalized fluorescence image $G_2'$ on the white-light image $G_1$.

A fluorescence image processing method by using the thus-configured fluoroscopy apparatus 1 according to this embodiment will be described hereinbelow.

Figure 5:
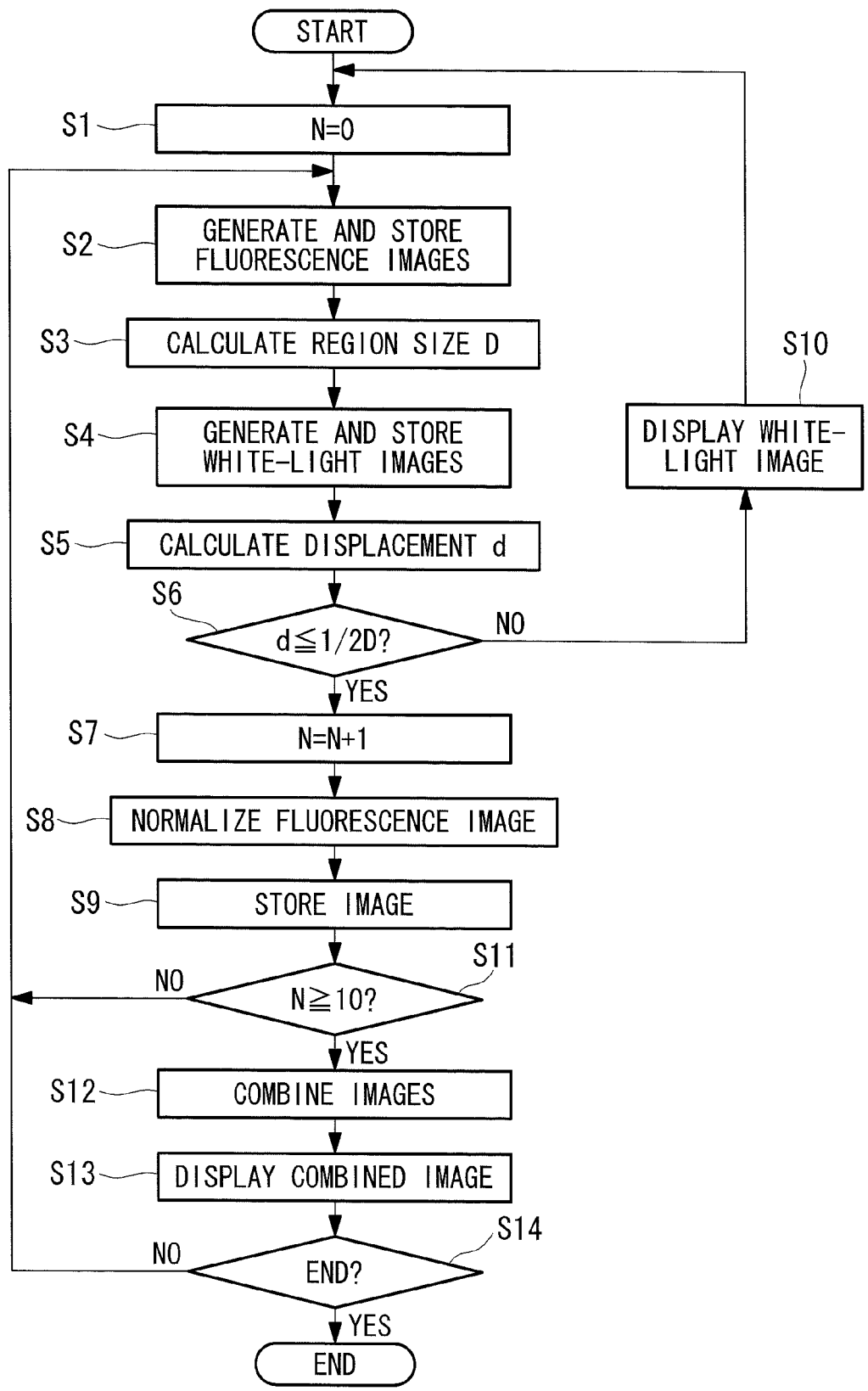
FIG. 5 is a diagram showing a flowchart explaining a fluorescence image processing method by the fluoroscopy apparatus in FIG. 1.

First, as shown in FIG. 5, a counter N is reset (step S1), and when fluorescence image signals are acquired by the image-acquisition device 15, the fluorescence images $G_2$ are generated by the fluorescence-image generating section 18 on the basis of the fluorescence image signals and are sequentially stored in the fluorescence-image storage section 20 (step S2).

The fluorescence images $G_2$ stored in the fluorescence-image storage section 20 are sent to the region-size calculating section 22. In the region-size calculating section 22, the fluorescence images $G_2$ sent from the fluorescence-image storage section 20 at 100-msec time intervals corresponding to the observation period are sequentially processed to extract the high-fluorescence-brightness region R, and the diameter D of the inscribed circle C is calculated as the size thereof (step S3).

On the other hand, when white-light image signals are acquired by the image-acquisition device 14, the white-light images $G_1$ are generated by the white-light-image generating section 17 on the basis of the white-light image signals and are sequentially stored in the white-light-image storage section 19 (step S4).

The white-light images $G_1$ stored in the white-light-image storage section 19 are sent to the displacement calculating section 21. The displacement calculating section 21 sequentially processes two continuous white-light images $G_1$ sent from the white-light-image storage section 19, acquired at 100-msec time intervals corresponding to the observation period, to extract feature points in the individual white-light images $G_1$ and calculates the distance between the same feature points of the two white-light images $G_1$.

Thus, the displacement d that indicates how much the observation target A has moved relative to the distal end face 2a of the inserted portion 2 while the two white-light images $G_1$ are acquired is calculated (step S5).

The displacement d calculated by the displacement calculating section 21 and the region size D of the high-fluorescence-brightness region R calculated by the region-size calculating section 22 are sent to the control unit 26.

In the control unit 26, the proportion of the displacement d to the sent region size D is calculated. If the proportion of the displacement d to the region size D, d/D, is ½ or less, the control unit 26 permits normalization computation by the normalization computing section 23 (step S6). When normalization computation is permitted by the control unit 26, the normalization computing section 23 increments the counter N (step S7) and normalizes the fluorescence image $G_2$ by dividing them by the white-light image $G_1$ (step S8). The generated normalized fluorescence image $G_2'$ is stored in the normalized-image storage section 25 (step S9), and thereafter, the processes from step S2 are repeated.

In contrast, if the proportion of the displacement d to the region size D, d/D, is higher than ½, the white-light image $G_1$ is displayed on the monitor 7 without performing the normalization computation, and the processes from step S1 are repeated (step S10).

The value of the counter N is continuously incremented during the repeated processes from step S2 unless the proportion of the displacement d to the region size D, d/D, exceeds ½, and it is determined whether the counter N=10, that is, whether the displacement d is small ten consecutive times (step S11). If the counter N=10, the image combining section 24 combines the normalized fluorescence image $G_2'$ with the white-light image $G_1$ (step S12), and the generated combined image G is displayed on the monitor 7 (step S13). Thereafter, the normalized fluorescence image $G_2'$ is combined with the white-light image $G_1$ as long as the counter N≧10 holds, that is, as long as the state in which the displacement d is small continues ten times or more, and the generated combined image G is displayed on the monitor 7. Then, it is determined whether to terminate the observation, and if it is to be continued, the processes from step S2 are repeated (step S14).

On the other hand, once the proportion of the displacement d to the region size D, d/D, exceeds ½ during the repetition of the processes from step S2, the display is switched to the display of only the white-light image $G_1$, and the process returns to step S1, where the counter N is reset.

Since fluoroscopy of biological tissue is performed by irradiating the biological tissue with excitation light, and reflected-light observation of the biological tissue is performed by irradiating the biological tissue with white light or the like, the time lag between the fluoroscopy and the reflected-light observation sometimes causes a shift between the captured fluorescence image and reflected-light image. The shift between the fluorescence image and the reflected-light image is caused by the pulsation of the biological tissue, a difference in exposure time, a relative positional shift between the fluoroscopy apparatus and the biological tissue, and so on. In this case, using the reflected-light image that has a shift relative to the fluorescence image to normalize the fluorescence image would result in incorrect normalization.

Thus, according to the fluoroscopy apparatus 1 and the fluorescence image processing method according to this embodiment, the positional shift between the fluorescence image $G_2$ and the white-light image $G_1$ used to normalize the fluorescence image $G_2$ is determined by using the displacement d of the white-light image $G_1$, and if the positional shift is large, normalization is not performed, and thus, a low-precision normalized fluorescence image $G_2'$ is not displayed, so that the problem of incorrect information being provided to the doctor or the like can be prevented.

Furthermore, since the normalized fluorescence image $G_2'$ is displayed only when the displacement d is small ten consecutive times, using the counter N, if the displacement d is large or if the state in which the displacement d is small does not continue, the normalized fluorescence image $G_2'$ is not displayed, so that a problem where the display switches between the combined image G and the white-light image $G_1$ in a short time (one second or less) can be prevented.

In this embodiment, although the observation period is set at 100 msec, and the combined image G is displayed only when the state in which the displacement d is small continues for ten observation periods, the present invention is not limited thereto; the observation period and the count of the counter N can be freely set.

Although the fluorescence image processing method according to this embodiment stops normalization of the fluorescence image $G_2$ if the proportion of the displacement d to the region size D, d/D, exceeds ½, the proportion d/D is not limited to ½ and can be freely set. For example, when the proportion d/D exceeds 1, that is, when the region size D is equal to the displacement d, the fluorescence image $G_2$ and the white-light image $G_1$ are considered not to overlap but to be completely shifted; thus, only in that case, normalization of the fluorescence images $G_2$ is stopped, and in the other cases, normalization may be permitted. This can reduce the period in which normalization of the fluorescence images $G_2$ is stopped.

Figure 6:
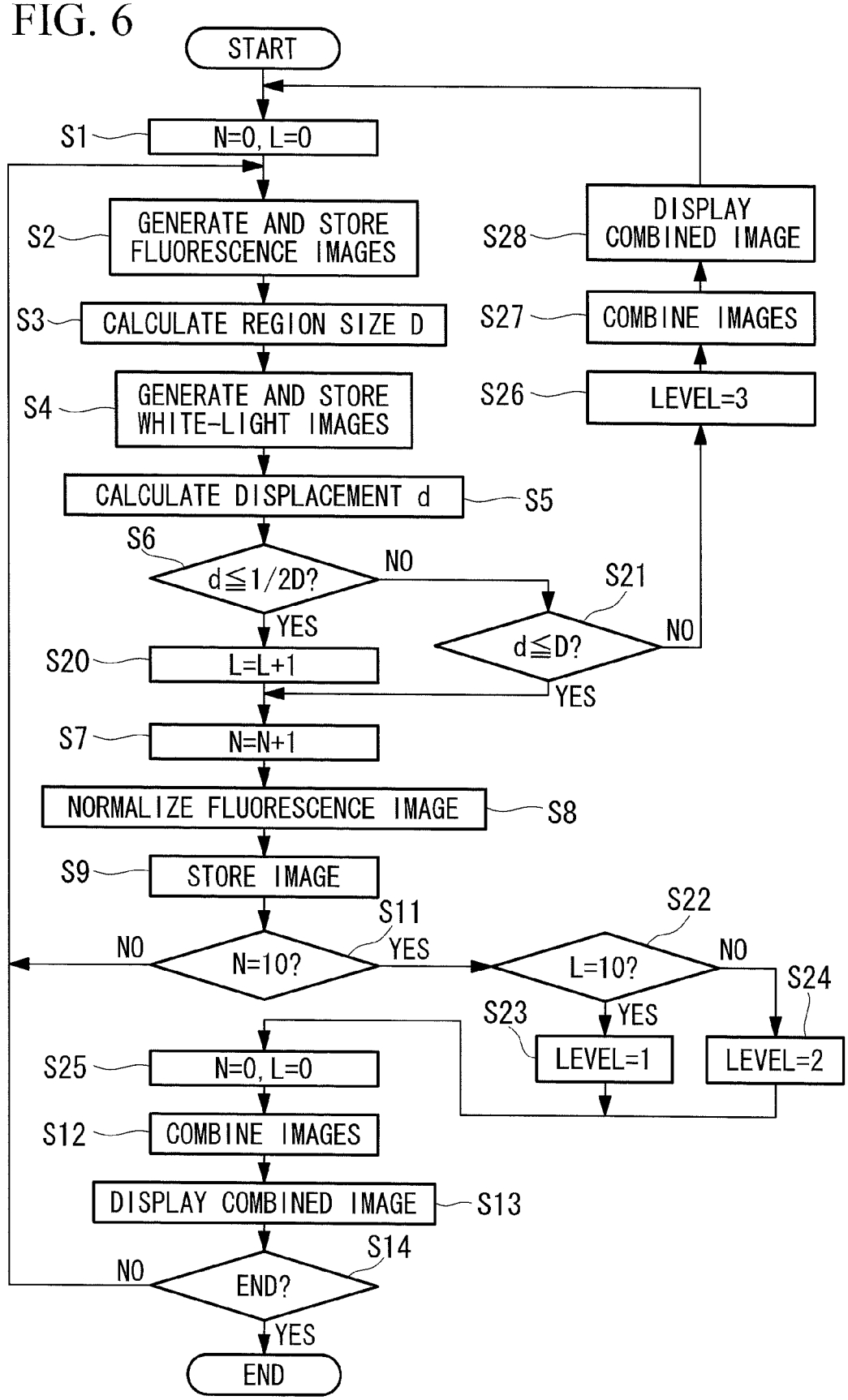
FIG. 6 is a diagram showing a flowchart for a first modification of the fluorescence image processing method in FIG. 5.
Figures 7, 8:
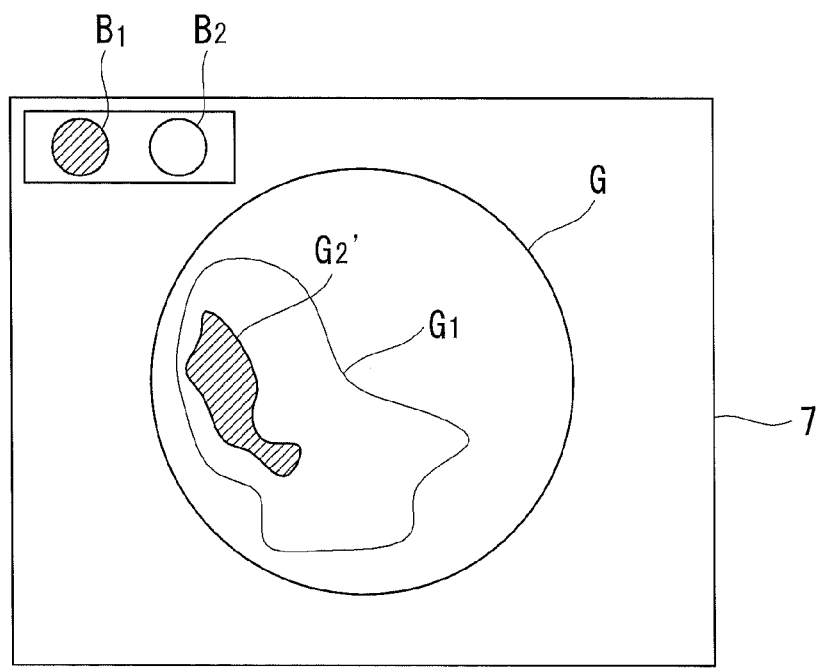
FIG. 7 is a diagram illustrating a display example of a combined image displayed on a monitor according to the fluorescence image processing method in FIG. 6.
FIG. 8 is a diagram showing a correlation table of normalization levels and threshold values stored in a control unit in a second modification of the fluorescence image processing method in FIG. 6.

In this case, information indicating the precision of normalization may be displayed together, as shown in FIGS. 6 and 7.

For example, the proportion of the displacement d to the region size D, d/D, may be divided into three, that is, ½ or less, higher than ½ and 1 or less, and higher than 1, and when all of the proportions d/D calculated during ten observation periods are ½ or less, the precision of normalization may be set to LEVEL 1, once the proportion is higher than 1, it may be set to LEVEL 3, and in the other cases, it may be set to LEVEL 2.

Specifically, in step S1, the counter N and a counter L are initialized, and if it is determined in step S6 that the proportion of the displacement d to the region size D, d/D, is ½ or less, the counters L and N are incremented (steps S20 and S7), and if it is determined that the proportion d/D is higher than ½ and 1 or less (step S21), only the counter N is incremented (step S7).

In both cases, normalization of the fluorescence image $G_2$ is performed (step S8), and the normalized fluorescence image $G_2$' is stored (step S9). If the counter N=10 in step S11, then it is determined whether the counter L=0 (step S22), and if the counter L=0, that is, the proportion d/D is always ½ or less for ten observation periods, the precision of normalization is set to LEVEL 1 (step S23), and in the other cases, that is, once the proportion d/D is higher than ½ and D or less, the precision of normalization is set to LEVEL 2 (step S24).

Thereafter, the counters N and L are reset (step S25), and the image combining section 24 combines the normalized fluorescence image $G_2$', the white-light image $G_1$, and information indicating the precision of normalization (step S12), and the generated combined image G is displayed on the monitor 7, as shown in FIG. 7 (step S13). Then, it is determined whether to terminate the observation, and if it is to be continued, the processes from step S2 are repeated (step S14).

In contrast, if it is determined in step S21 that the proportion d/D is higher than 1, the precision of normalization is set to LEVEL 3 (step S26), the white-light image $G_1$ and information indicating that the precision of normalization is at LEVEL 3 are combined (step S27), and the generated combined image G is displayed on the monitor 7 (step S28).

In the example shown in FIG. 7, if the precision of normalization is at the highest LEVEL 1, two circular indicators $B_1$ and $B_2$ are both turned on, if it is at LEVEL 2, only one indicator $B_1$ is turned on, and if it is at LEVEL 3, no indicator is turned on. FIG. 7 shows a state at LEVEL 2 in which only one indicator $B_1$ is turned on. The method of displaying the precision of normalization is not limited to the example in FIG. 7 and can be any method. Instead of displaying the precision of normalization on the monitor 7, it may be announced using sound or the like.

Thus, announcing the information indicating the precision of normalization allows a doctor or the like to recognize whether the control unit has stopped normalization of the fluorescence image. Additionally, since the displacement between the fluorescence image and the white-light image increases, so that the precision of normalization decreases as the positional shift of the observation target A increases relative to the size of the high-fluorescence-brightness region R, announcing the precision calculated by the control unit 26 by using the monitor 7 allows the reliability of the normalized fluorescence image $G_2$' to be recognized by the doctor or the like.

Figure 9:
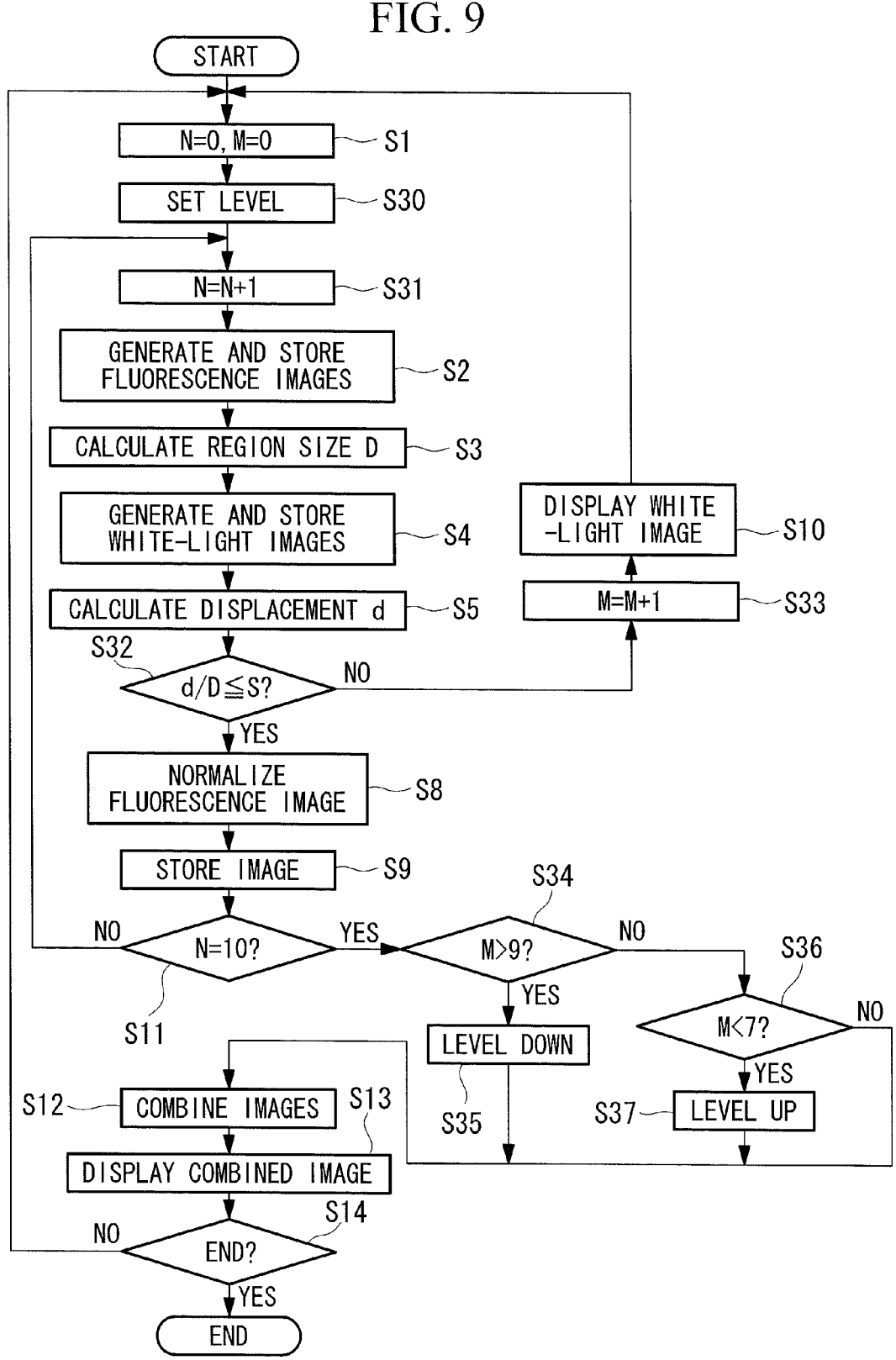
FIG. 9 is a diagram showing a flowchart explaining the fluorescence image processing method in FIG. 8.

As shown in FIGS. 8 and 9, a threshold value for the control unit 26 to perform normalization may also be changed depending on the precision of normalization. That is, when observation is started, the counters N and M are initialized in step S1, and then the level of normalization precision is set (step S30). The control unit 26 stores the levels of normalization precision and threshold values S in association with each other, as shown in FIG. 8, and in the first setting, the level of normalization precision is set to LEVEL 1 at which the most strict threshold value S is set. At that time, the threshold value S is 0, for example.

Next, the counter N is incremented (step S31), the fluorescence images $G_2$ are generated and stored (step S2), the region size D is calculated (step S3), the white-light images $G_1$ are generated and stored (step S4), the displacement d is calculated (step S5), and it is determined whether the displacement d relative to the region size D is the threshold value S or less (step S32).

If the proportion of the displacement d to the region size D, d/D, is lower than or equal to the threshold value S, the fluorescence image $G_2$ is normalized (step S8), the normalized fluorescence image $G_2$' is stored (step S9), and steps S31 to S9 are repeated until the counter N reaches 10.

In contrast, if the proportion of the displacement d to the region size D, d/D, is higher than the threshold value S, the fluorescence image $G_2$ is not normalized, the counter M is incremented (step S33), and after the white-light image $G_1$ is displayed (step S10), steps S1 to S9 are repeated until the counter N reaches 10.

After completion of step S9, it is determined whether the counter N=10 (step S11), and if the counter N=10, it is determined whether a counter M is greater than 9 (step S34), and if M>9, that is, no normalization is performed during ten iterations, the level of normalization precision is decreased by one (step S35). In this example, the initial LEVEL 6 is changed to LEVEL 5.

Since this allows the normalization to remain stopped when the positional shift between the fluorescence image $G_2$ and the white-light image $G_1$ is large, the proportion for stopping the normalization can be relaxed, so that a normalized fluorescence image $G_2$', even with low precision, can be acquired.

On the other hand, it is determined in step S34 whether the counter M is smaller than 7 (step S36), and if M<7, that is, four or more normalizations are performed during ten iterations, the level of normalization precision is increased by one (step S37). If the level is the highest, the level is not raised further.

The image combining section 24 combines the normalized fluorescence image $G_2$', the white-light image $G_1$, and information indicating the precision of normalization (step S12), and the generated combined image G is displayed on the monitor 7 (step S13). Then, it is determined whether to terminate the observation, and if it is to be continued, the processes from step S31 are repeated (step S14).

This allows the normalization computation to be performed always at a constant time rate, thus allowing a normalization computation suitable for the observation environment.

For the values shown in FIG. 8, associating the level of normalization precision and the threshold value S, which are stored in the control unit 26, two or more kinds of pattern may be stored, from which a pattern suitable for the observation conditions can be selected with a touch switch or the like provided on the monitor 7. The inserted portion 2 of the endoscope may be connected to the image processing unit 6 so that an ID (identifying code) built into the inserted portion is sent to the control unit 26 so that a pattern suitable for the inserted portion used can be selected.

The present invention provides the advantage of preventing incorrect information from being given to a doctor even if a positional shift has occurred between a fluorescence image and a reflected-light image, thereby avoiding a mistaken diagnosis.

REFERENCE SIGNS LIST

1 fluoroscopy apparatus
7 monitor (normalization-stop announcing section, normalization-precision announcing section)
17 white-light-image generating section
18 fluorescence-image generating section
21 displacement calculating section
22 region-size calculating section
23 normalization computing section (fluorescence-image correcting section)
26 control unit (normalization-precision calculating section, stop-ratio calculating section)
A observation target
d displacement
D region size (size)
$G_1$ white-light image
$G_2$ fluorescence image
R high-fluorescence-brightness region (region)
S2 fluorescence-image generation step
S3 region-size calculation step
S4 white-light image-generation step
S5 displacement calculation step
S9 normalization step (fluorescence-image correction step)

The invention claimed is:

1. A fluoroscopy apparatus comprising:
   a white-light-image generating section that generates a white-light image from a signal obtained by image-capturing reflected light of white light that irradiates an observation target;
   a fluorescence-image generating section that generates a fluorescence image from a signal obtained by image-capturing fluorescence generated by irradiation of the observation target with excitation light;
   a fluorescence-image correcting section that normalizes the fluorescence image generated by the fluorescence-image generating section by using the white-light image generated by the white-light-image generating section;
   a displacement calculating section that calculates the displacement of the observation target in the white-light image by processing a plurality of the white-light images generated by the white-light-image generating section from signals obtained by image-capturing at time intervals;
   a region-size calculating section that calculates the size of a region having a fluorescence intensity higher than or equal to a predetermined threshold value by processing the fluorescence image generated by the fluorescence-image generating section; and
   a control unit that controls the fluorescence-image correcting section so that normalization of the fluorescence image is stopped when the displacement of the observation target calculated by the displacement calculating section relative to the size of the region calculated by the region-size calculating section is higher than or equal to a predetermined proportion.

2. The fluoroscopy apparatus according to claim 1, comprising a normalization-stop announcing section that, when the control unit has stopped normalization of the fluorescence image by the fluorescence-image correcting section, announces that fact.

3. The fluoroscopy apparatus according to claim 1, comprising:
   a normalization-precision calculating section that calculates a precision of normalization by the fluorescence-image correcting section on the basis of the size of the region calculated by the region-size calculating section and the displacement of the observation target calculated by the displacement calculating section; and
   a normalization-precision announcing section that announces the precision of normalization calculated by the normalization-precision calculating section.

4. The fluoroscopy apparatus according to claim 1, comprising:
   a stop-ratio calculating section that calculates the ratio of time during which normalization of the fluorescence image by the fluorescence-image correcting section is stopped by the control unit,
   wherein the control unit adjusts the proportion on the basis of the ratio of a normalization stop time calculated by the stop-ratio calculating section.

5. A fluorescence image processing method, comprising:
   a white-light-image generation step of generating a white-light image from a signal obtained by image-capturing reflected light of white light that irradiates an observation target;
   a fluorescence-image generation step of generating a fluorescence image from a signal obtained by image-capturing fluorescence generated by irradiation of the observation target with excitation light;
   a region-size calculation step of calculating the size of a region having a fluorescence intensity higher than or equal to a predetermined threshold value by processing the fluorescence image generated in the fluorescence-image generation step;
   a displacement calculation step of calculating the displacement of the observation target in the white-light image by processing a plurality of white-light images generated from signals obtained by image-capturing at time intervals; and
   a fluorescence-image correction step of normalizing the fluorescence image by using the white-light image only when the displacement of the observation target calculated in the displacement calculation step relative to the size of the region calculated in the region-size calculation step is lower than a predetermined proportion.

* * * * *